United States Patent
Cekov et al.

(10) Patent No.: US 8,251,583 B2
(45) Date of Patent: Aug. 28, 2012

(54) REMOVABLE RADIATION SENSOR FOR DENTAL IMAGING SYSTEMS

(75) Inventors: Lyubomir L. Cekov, Rolling Meadows, IL (US); Arkady Kantor, Buffalo Grove, IL (US); Donald Walker, Mundelein, IL (US); Alan P. Krema, Naperville, IL (US)

(73) Assignee: Midmark Corporation, Versailles, OH (US)

( * ) Notice: Subject to any disclaimer, the term of this patent is extended or adjusted under 35 U.S.C. 154(b) by 360 days.

(21) Appl. No.: 12/638,611

(22) Filed: Dec. 15, 2009

(65) Prior Publication Data

US 2011/0142198 A1    Jun. 16, 2011

(51) Int. Cl.
  A61B 6/14    (2006.01)
  H05G 1/64    (2006.01)
  H05G 1/02    (2006.01)
  H05G 1/08    (2006.01)
(52) U.S. Cl. .................. 378/191; 378/38; 378/98.8
(58) Field of Classification Search .............. 378/38–40, 378/98.8, 113–117, 189–191, 195–198, 205, 378/210
See application file for complete search history.

(56) References Cited

U.S. PATENT DOCUMENTS

| | | | |
|---|---|---|---|
| 4,741,007 A | 4/1988 | Virta et al. | |
| 5,425,065 A | 6/1995 | Jarvenin | |
| 5,511,106 A | 4/1996 | Doebert et al. | |
| 5,732,119 A | 3/1998 | Kopsala | |
| 6,219,401 B1 * | 4/2001 | Tachibana et al. | 378/39 |
| 6,466,641 B1 | 10/2002 | Virta et al. | |
| 6,510,196 B2 | 1/2003 | Laner | |
| 6,553,095 B2 | 4/2003 | Rinaldi et al. | |
| 6,731,717 B2 | 5/2004 | Kopsala | |
| 6,744,847 B2 | 6/2004 | Martti | |
| 6,829,326 B2 | 12/2004 | Woods et al. | |
| 6,891,921 B2 | 5/2005 | Kopsala | |
| 7,103,141 B2 * | 9/2006 | Sonobe et al. | 378/39 |
| 7,581,883 B2 * | 9/2009 | Kato | 378/167 |
| 7,629,587 B2 * | 12/2009 | Yagi et al. | 250/370.15 |
| 7,889,843 B2 * | 2/2011 | Watanabe | 378/116 |

* cited by examiner

Primary Examiner — Thomas R Artman
(74) Attorney, Agent, or Firm — Wood, Herron & Evans, LLP

(57) ABSTRACT

A removable radiation sensor for connecting to a panoramic dental radiation imaging system. The sensor includes a radiation sensor unit mounted in a housing. Connector bearings are positioned within the housing so as to engage with a pair of connector pins provided as part of the upright support of the imaging system. A lock pin within the housing is selectively slidable between Locked and Unlocked, and biased toward Locked. The lock includes a locking pin with a groove, and when the groove is aligned with the respective connector pin, the lock is unlocked, and that connector pin is slidable axially within the bearings. When the groove is not aligned with the connector pin, the lock is locked, the locking pin engaging with a groove formed for that purpose in the connector pin. The sensor has a field-replaceable electrical connector, to reduce maintenance cost.

17 Claims, 11 Drawing Sheets

REMOVABLE RADIATION SENSOR FOR DENTAL IMAGING SYSTEMS

BACKGROUND OF THE INVENTION

This invention relates to dental radiation imaging systems, and in particular to systems having a removable radiation detector so as to permit varied uses of the detector.

Panoramic and cephalometric dental radiation imaging is used to obtain images of a patient's teeth and jaws. Radiation imaging is essential in providing accurate information in the diagnostic process. Imaging techniques, such as bitewing (interproximal), edentulous (toothless), full mouth series, occlusal, periapical, panoramic techniques, and others, provide information in discovering tooth decay, broken fillings, tumors, occlusal trauma, and other effects that would otherwise be unseen by the eye, whether located inside the teeth, between the teeth, or below the gum line, within the gum tissue. In general, the radiological examinations in dentistry may be classified as intraoral and extraoral, determined by where the radiation sensor is placed with respect to the mouth.

In intraoral radiological examinations, the sensor is placed inside of the mouth, and used to acquire a radiation image of a limited, small region with the greatest possible level of detail. In the extraoral radiological examinations, the sensor is positioned outside of the mouth, and used to acquire a radiation image of a far larger region of the human/animal teeth, jaw, and head. In dentistry, common extraoral imaging is divided into two types. Panoramic radiation imaging shows an area, curved following more or less the mandible shape, of the whole maxillo-facial block. Cephalometric radiation imaging shows a projection, as parallel as possible, of the whole or part of the skull. And three-dimensional techniques have been introduced recently.

Extraoral imaging apparatus employs techniques that aim to move the radiation source, the radiation sensor, or both, in relation to the imaged object, thru a desired trajectory, in such a way as to reveal the anatomic structure of interest and ideally to blur the artifacts from non-related radio-opaque structures, such as bones, even though the radiation energy has also been obstructed by those structures. The goal is to produce a radiation image that meets quality criteria, such as showing undistorted anatomic shapes (constant size and the same magnification in both horizontal and vertical direction, orthogonally of the radiation beam) with uniform contrast and enough resolution to reveal the smallest details of interest.

For example, the general Orthopantomogram (also referred to as OPG, panorex, or pano) employs a rotation technique where the center of rotation is moved during the image acquisition in order to reveal the upper and lower jaws (including teeth, bone structure beneath the teeth and the temporomandibular joint (TMJ)) on the produced two-dimensional view. In addition, the cephalometric imaging attachment employs combination of linear and rotation movement, but in order to show a projection, as parallel as possible, of the whole skull.

The first Orthopantomogram device was developed in 1951, and the first manufacturing of such devices was begun in 1964 by Instrumentarium. Since than, companies such as Planmeca, Carestream Health (formerly Kodak), Gendex, Instrumentarium Dental, Sirona, Sorodex, and others manufacture various devices for panoramic and cephalometric radiation imaging. Many extraoral radiation devices, such as the Planmeca ProOne™, Kodak 8000, Gendex Orthoralix™ 8500 DDE, and the Sirona Orthophos™ 3 DS, do not have cephalometric capabilities. Others, such as the Kodak 9000C, provide cephalometric capabilities, but do not have a transferable sensor.

Many dental and surgical offices require both types of imaging systems, and offices requiring both types of imaging systems had been required to purchase both systems. The radiation sensors for panoramic and cephalometric imaging systems are very costly components, and thus greatly increase the overall cost of the systems. A sensor which is transferable between a panoramic and cephalometric system would thus provide a very advantageous cost savings to a user of both systems. A third group of devices, such as Planmeca ProMax™, Gendex Orthoralix™ 9200 AEC, Instrumentarium Dental Orthoceph™ OC200 D, and Sirona Orthophos™ XG, do have cephalometric capabilities and a transferable sensor. Those systems, however, employ connection systems that are complicated, less reliable, and/or expensive.

Further, most of the commonly used connectors in those systems have limited durability, on the order of 500 insertions. A very few connectors could reach 10,000 insertions. This durability sometimes is not enough for the long term usage of certain extraoral X-Ray devices, especially because of the usual long lifespan of more than ten years. Thus, most of the sensors on the market employ custom connectors with spring-loaded contacts to provide the needed maximum durability and reliability, as well as low resistance and capacitance for high-speed data transfer. That choice, however, adds cost to the sensor, and limits the sensor connector only to the essential data signals and power lines.

The present invention relates to improvements to the apparatus described above and to solutions to some of the problems raised or not solved thereby.

SUMMARY OF THE INVENTION

A need exists, therefore, for a radiation imaging system which has a sensor that is easily movable between a panoramic dental radiation imaging application and a cephalometric dental radiation imaging application and can be firmly secured in place in both applications. Objects of such a connector/attachment system include providing a low resistance and capacitance connection for high-speed data transfer, and high current capabilities for the power supply; the ability to be durable and reliable; the ability to provide precise and secure sensor attachment that does not introduce image distortion as result of mechanical movement; the ability to allow easy sensor attachment and detachment; the ability to provide meaningful sensor position detection; and the ability to provide additional manufacturing/diagnostic functionality, such as testing and programming interfaces. Further, the novel approach provided by the present invention also uses a high quality, high-speed connector, such as an MDR connector, although the solution is not limited only to this type of connector, with a stated durability of 10,000 insertions or more. That is enough for the most common usages of the sensor. As a further enhancement, the present invention also provides easy in-the-field replacement of the connector, if the sensor connector does happen to wear out. This approach decreases the overall cost and allows adding manufacturing/diagnostic capabilities to the sensor connector.

The present invention relates to panoramic and cephalometric dental radiation imaging, and in particular to a radiation sensor which is movable between both types of systems, the sensor being easily removable from and connectable to each system, and firmly secured in place in each system. The invention provides a removable radiation sensor for being removably connected to a panoramic dental radiation imaging system, having a radiation source supported by an upright support. The removable radiation sensor includes a sensor housing and a radiation sensor unit mounted within the housing. Connector bearings are mounted within the housing and sized and positioned therein so as to engage with a pair of connector pins provided for that purpose as part of the upright support. A lock is mounted within the housing and selectively slidable between a locked position and an unlocked position. The lock includes a locking pin positioned within the housing transverse to the connector bearings, and therefore also transverse to the connector pins when the sensor is mounted to the upright support. The locking pin has a groove formed about the periphery of one end thereof, so that when the groove is aligned with one of the connector pins, that connector pin is slidable axially within the bearings, and the locking pin is thus in the unlocked position. When the groove is not aligned with the connector pin, the locking pin engages with a groove formed for that purpose in the connector pin, and the locking pin is therefore in the locked position, preventing the connector pin from sliding axially. A biasing spring is provided for biasing the locking pin toward the locked position.

Other objects and advantages of the invention will become apparent hereinafter.

DETAILED DESCRIPTION

This application is being filed at the same time as a patent application on a patient positioning system for a panoramic dental radiation imaging system, and a patent application on a motion system for a dental imaging system, and a design patent application on a dental imaging system, all filed on the same day as this application and assigned to the same assignee. The disclosure of each of those other patent applications is incorporated herein by reference.

Figure 1:
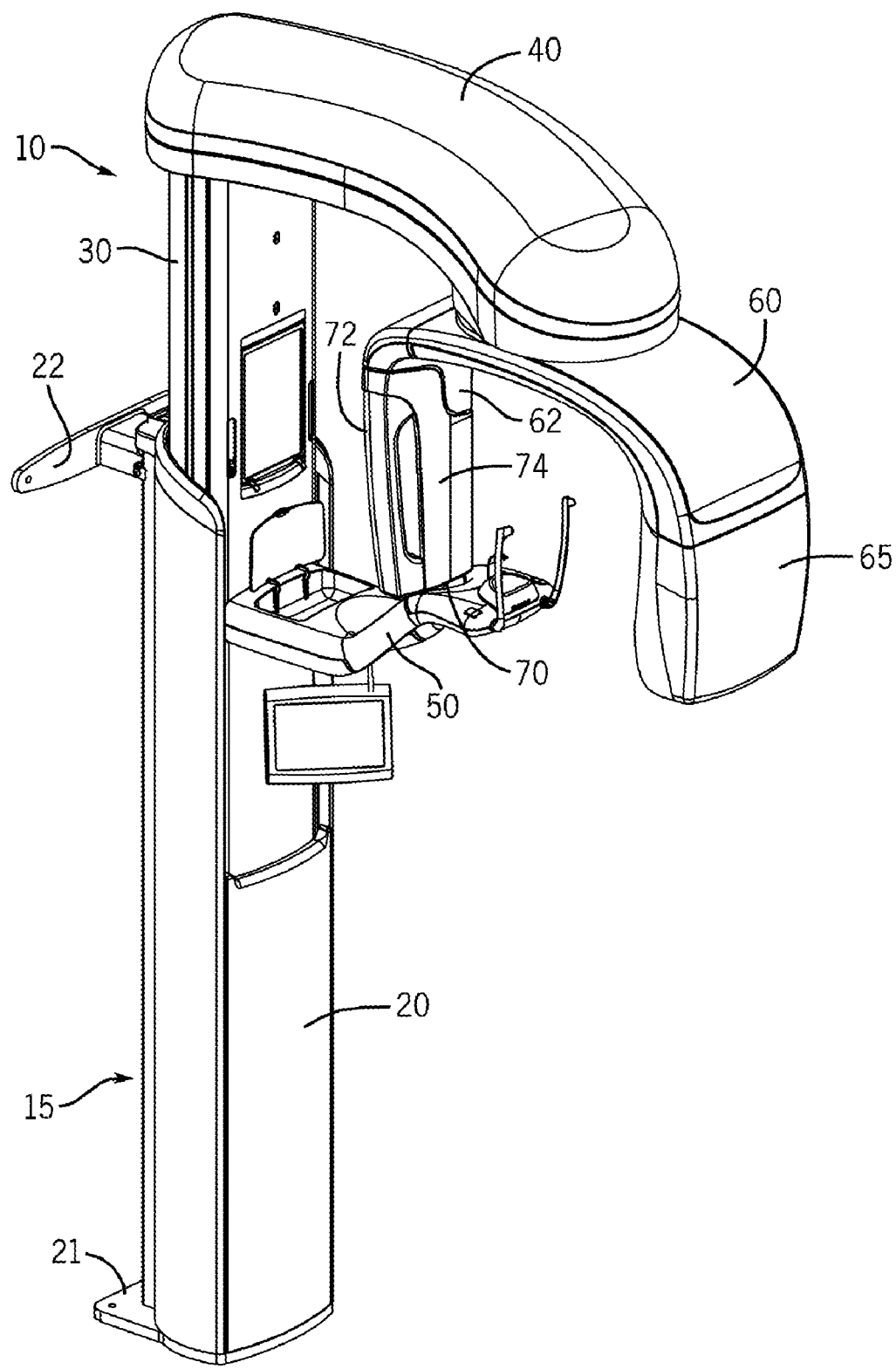
FIG. 1 is a perspective view of a panoramic dental radiation imaging machine in accordance with one embodiment of the present invention.

One embodiment of a panoramic dental radiation imaging system 10 with a removable radiation sensor body 70, having a radiation sensor unit 71 inside, is shown in FIG. 1. While the invention may be susceptible to embodiment in different forms, there is shown in the drawings, and herein will be described in detail, certain illustrative embodiments with the understanding that the present disclosure is to be considered an exemplification of the principles of the invention, and is not intended to limit the invention to those as illustrated and described herein. Additionally, features illustrated and described with respect to one embodiment could be used in connection with other embodiments.

Figure 2:
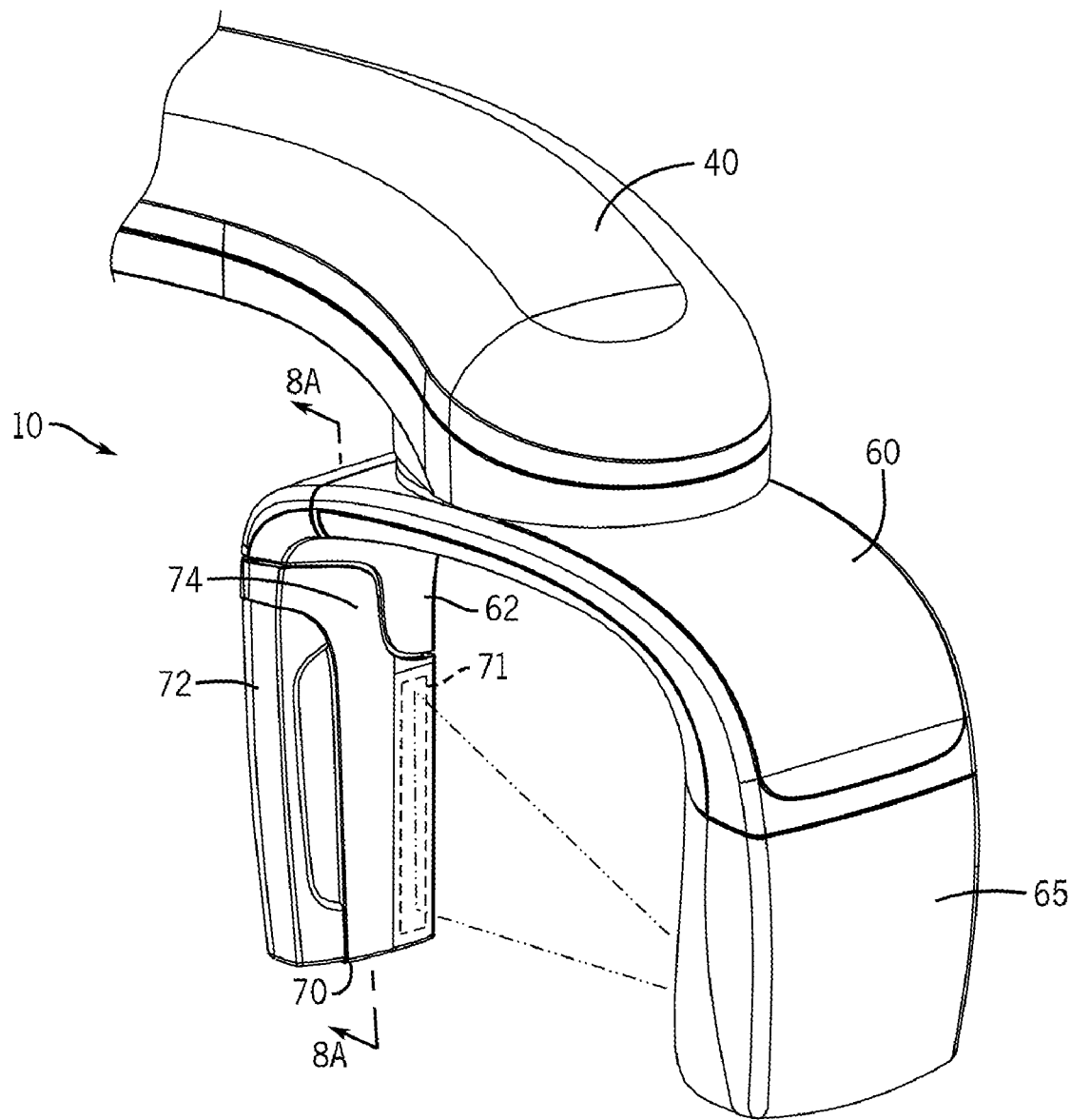
FIG. 2 is a perspective view of a C-arm portion of a panoramic dental radiation imaging machine.

FIGS. 1 and 2 show a panoramic dental radiation imaging system 10. The imaging system 10 is used for imaging of a dental patient's teeth, and generally includes an upright support 15 for supporting a radiation source 65 and a radiation sensor 71 positioned inside a removable radiation sensor body 70. In the most preferred embodiment shown, upright support 15 is formed of an outer column 20, an inner column 30 capable of telescoping within the outer column, an overhead arm 40 rotatably fixed atop the inner column, a C-arm 60 rotatably connected to the distal end of the overhead arm, and a patient positioning arm 50 mounted to the inner column. Upright support 15, by means of outer column 20, may be fixed to a floor and/or a wall by a floor support foot 21 and/or a wall support leg 22 to support the radiation system 10. As shown in the figures, according to the present invention, the radiation sensor body 70 is removable from and re-connectable to upright support 15, in this embodiment by means of being removably connected to the C-arm 60.

In a preferred embodiment, sensor body 70 is comprised of a handle 72 and a housing 74. Handle 72 allows a user to easily and firmly grasp sensor body 70 for removal from and attachment to radiation systems. A connection system, including a physical connection sub-system and an electrical connection sub-system, couples sensor body 70 to mounting portion 62 of C-arm 60. As to the physical connection system, sensor body 70 is locked in place on C-arm 60 by means of a locking mechanism, in which mounting portion 62 of C-arm 60 has a top connector pin 64 and bottom connector pin 66 coupled thereto. Bottom connector pin 66 includes a neck 67 which allows sensor body 70 to be removably locked to, and removed from, C-arm 60.

Figure 5:
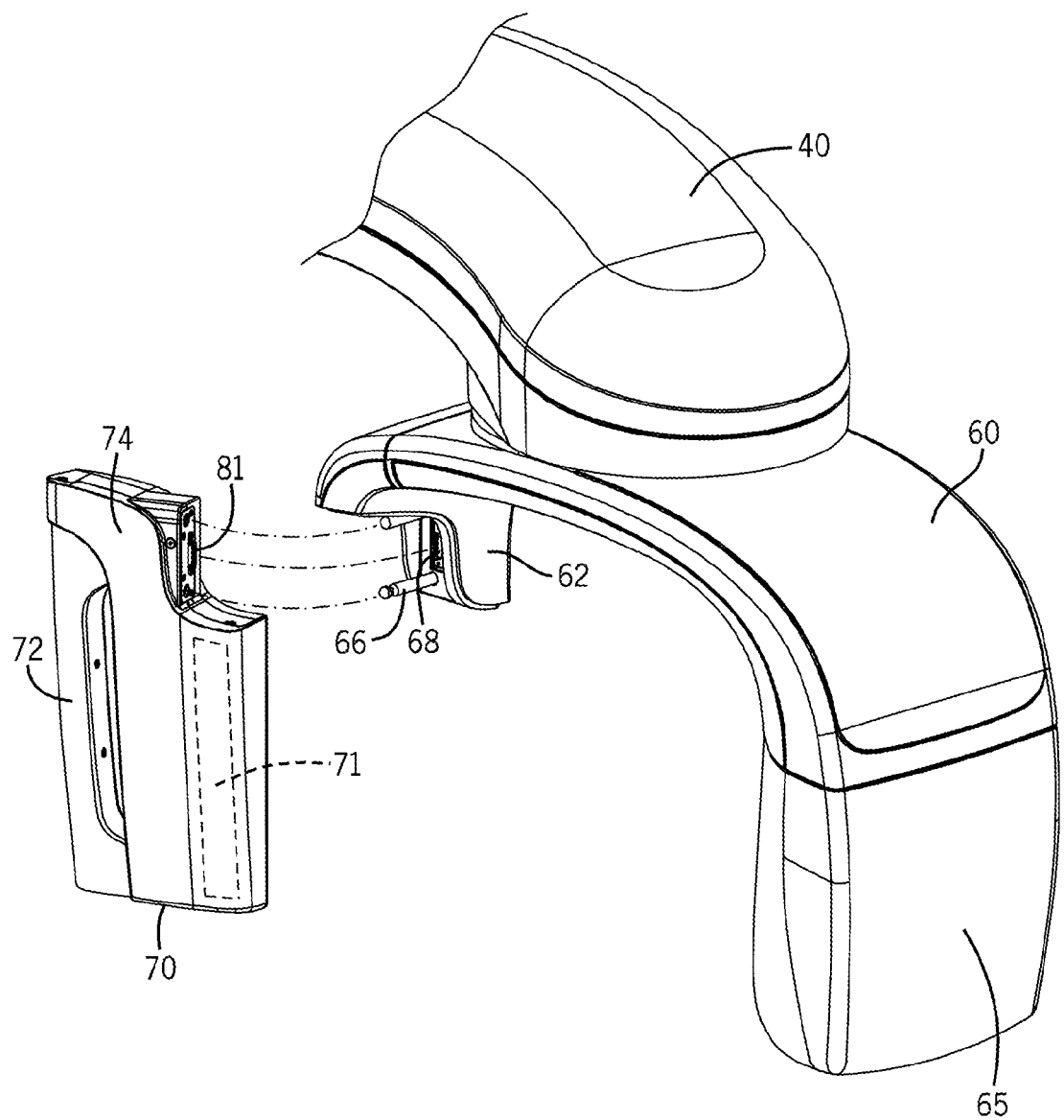
FIG. 5 is a perspective view of a C-arm portion of a panoramic dental radiation imaging machine with a removable sensor detached from the C-arm.
Figure 6A:
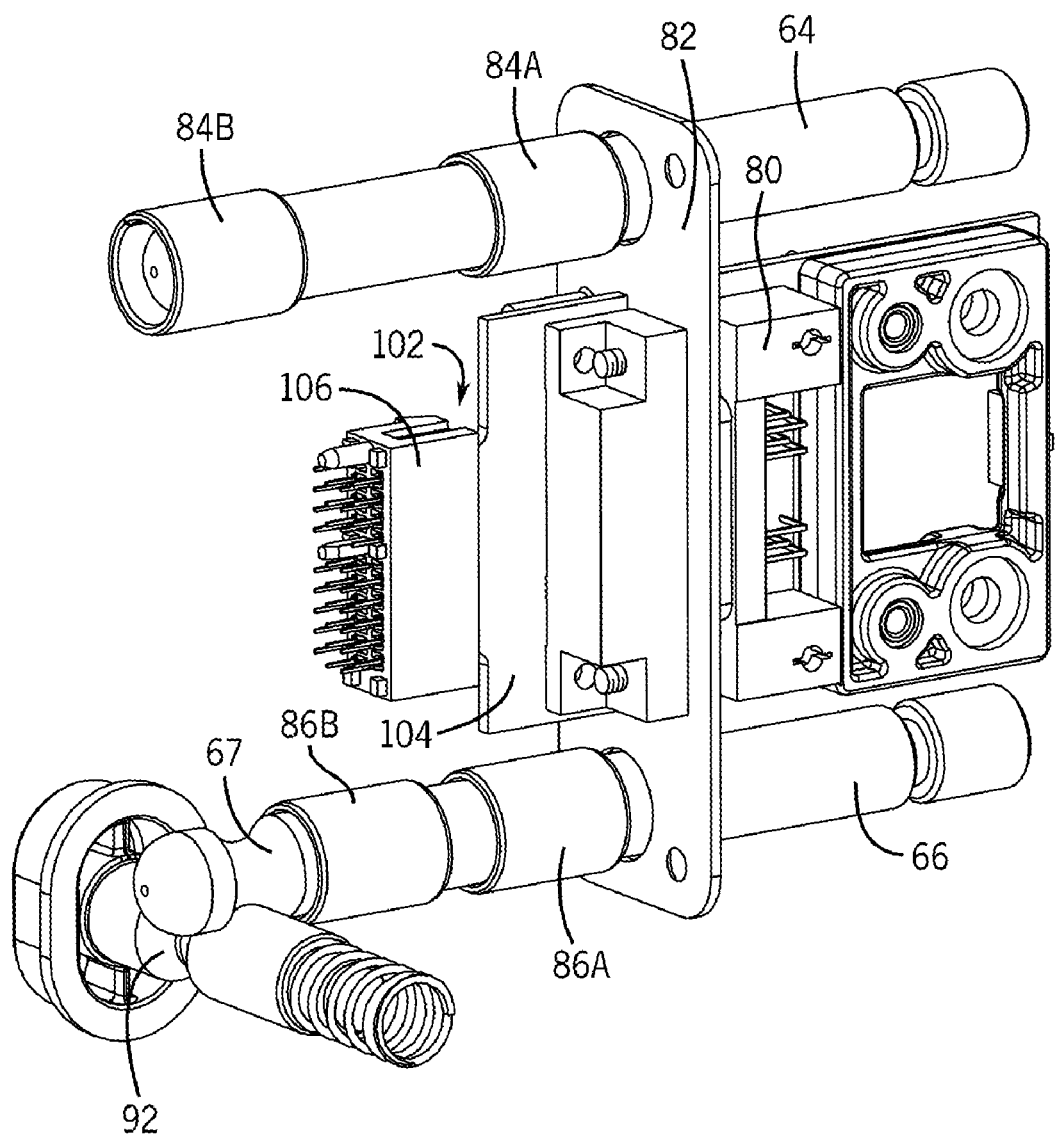
FIG. 6A is a perspective view of a C-arm portion of a panoramic dental radiation imaging machine, with covers and certain parts removed to show detail as to how the removable sensor is attached to the C-arm portion of the panoramic dental radiation machine.
Figure 6B:
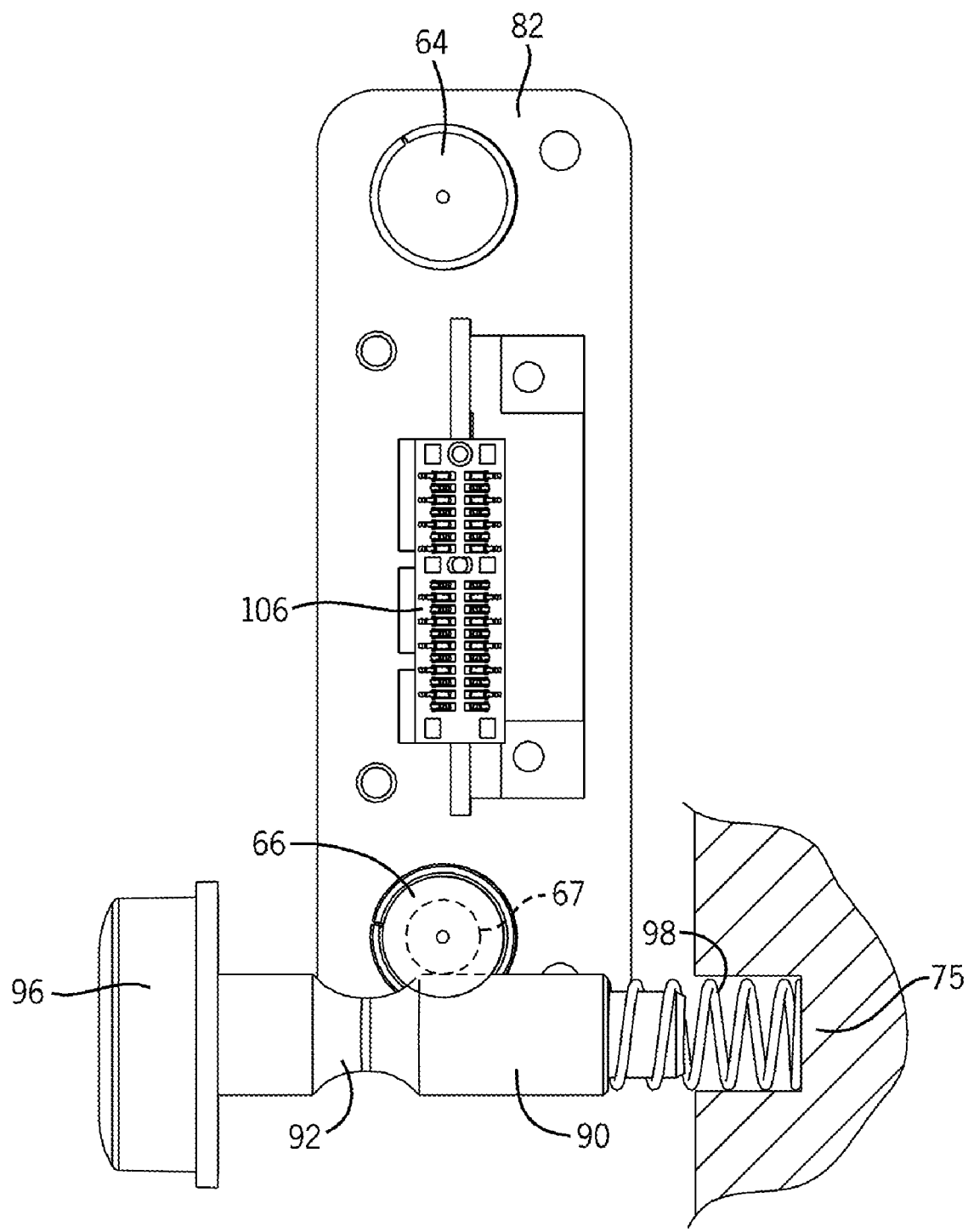
FIG. 6B is an end elevation view of the portion and parts shown in FIG. 6A.

As seen in FIGS. 5, 6A and 6B, in the most preferred embodiment as shown, mounting plate 82 is coupled to sensor housing 74, and openings 82A, 82B in mounting plate 82 receive top connector pin 64 and bottom 66 connector pin of C-arm 60. An additional void in mounting plate 82 is provided through which an electronic connector 81 passes for connection to matching connector 68 of C-arm 60, as will be explained in more detail below. Top connector bearings 84A, 84B coupled to sensor housing 74 receive top connector pin 64 when sensor body 70 is attached to C-arm 60. Similarly, bottom connector bearings 86A, 86B receive bottom connector pin 66. Top connector bearings 84A, 84B and bottom connector bearings 86A, 86B ensure proper alignment of top connector pin 64 and bottom connector pin 66 in the sensor housing 74, as well as stabilize the pins 64, 66 when sensor body 70 is attached to C-arm 60.

Figure 7A:
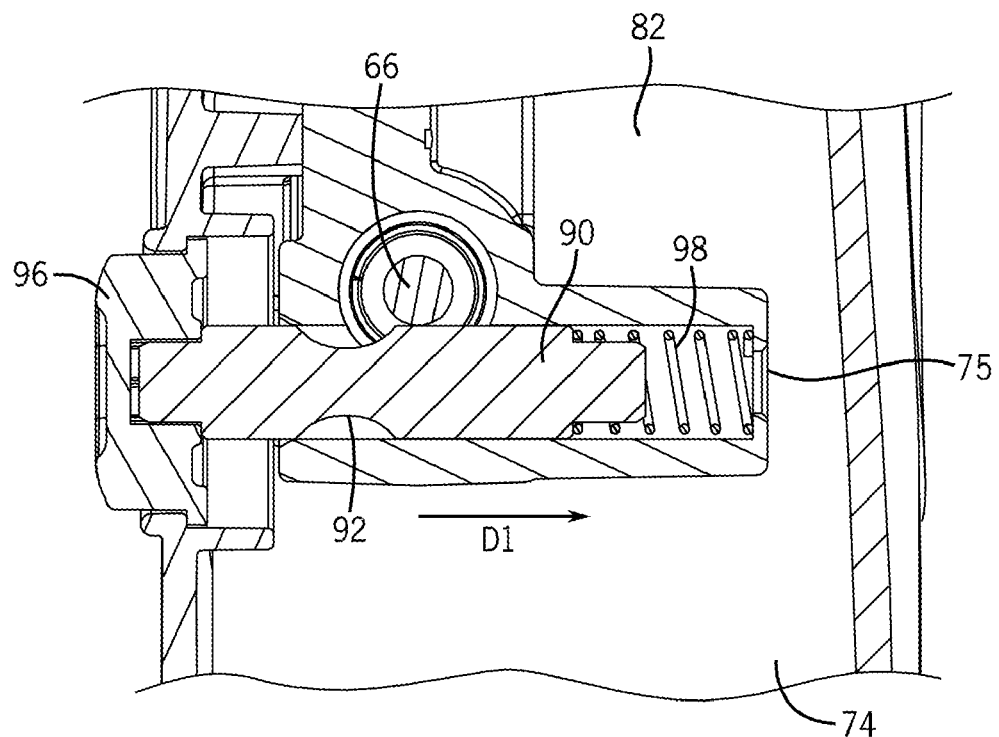
FIG. 7A is a detail view of a locking pin and a bottom connector pin with sensor secured to C-arm and locking pin and button in default position.
Figure 7B:
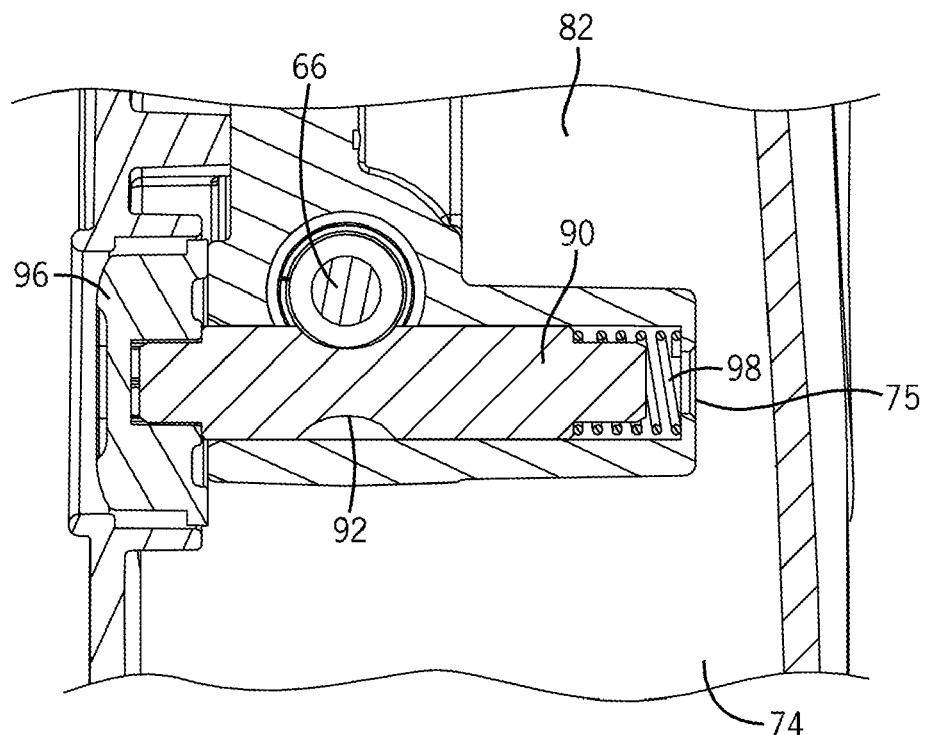
FIG. 7B is a detail view of a locking pin and bottom connector pin with button depressed and locking pin in position for detachment of sensor from C-arm.

The locking mechanism includes a locking pin 90 as shown in FIGS. 6A, 6B, 7A and 7B which engages with bottom connector pin 66 at neck 67. This engagement holds sensor body 70 securely in place on C-arm 60, and also ensures that sensor body 70 is properly positioned on C-arm 60, i.e. ensures that the sensor body 70 is not pushed too far onto connector pins 64, 66, and that electronic connector 81 is not pushed too far into or onto matching connector 68. To release the sensor body 70 from the C-arm 60, a user pushes a button 96 on sensor housing 74. Button 96 is coupled to locking pin 90, which is spring-loaded against an opening 75 provided for that purpose in opposing side of housing 74 by any suitable biasing mechanism, such as a biasing spring 98, shown in the embodiment of the figures as a coil spring. Thus, when button 96 is pushed against the force of spring 98, the button and locking pin 90 then move in direction D1 shown in FIG. 7A until a groove 92 formed for that purpose in the locking pin is aligned with bottom connector pin 66, as shown in FIGS. 6A and 7B. Groove 92 allows bottom connector pin 66 to disengage from locking pin 90, allowing sensor body 70 to be pulled away from C-arm 60 and detached from the C-arm as shown in FIG. 5. When button 96 is released, the biasing force of spring 98 moves the button and the locking pin 90 back to the extended position (FIG. 7A) such that the spring 98 is extended. To re-attach sensor body 70, connector pins 63 and 66 are inserted into openings 82A, 82B in mounting plate 82, the button 96 is pushed, the groove 92 is again aligned with the connector pin 66, the sensor body is slid the rest of the way onto the connector pins 64, 66, the neck 67 of the bottom connector pin 66 is aligned with the locking pin 90, and the button is released. This action locks the locking pin 90 onto the connector pin 66, and thereby the sensor body 70 onto the C-arm 60.

Figure 3:
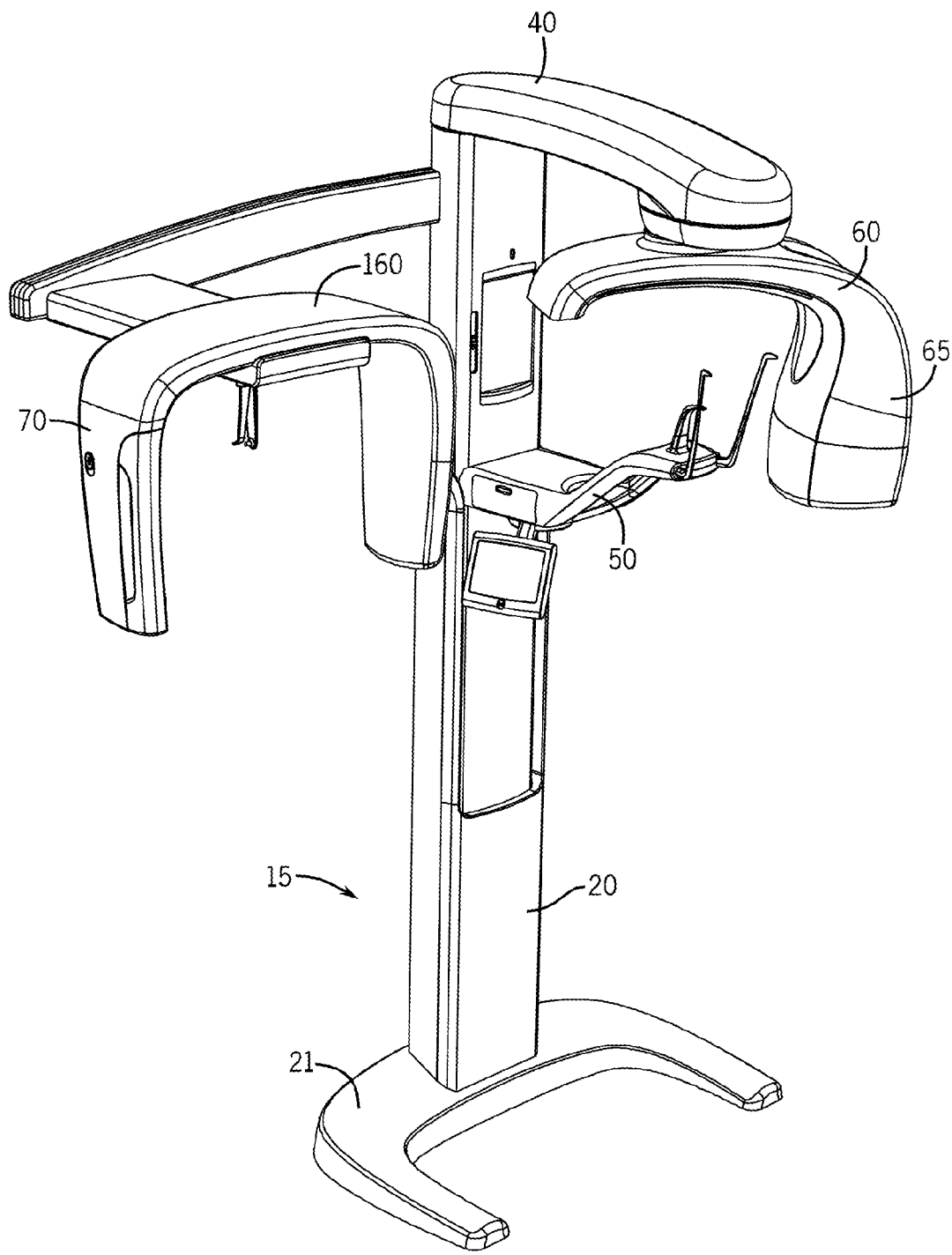
FIG. 3 is a perspective view of a dental radiation imaging machine with attachments for a removable sensor in a panoramic application and in a cephalometric application.
Figure 4:
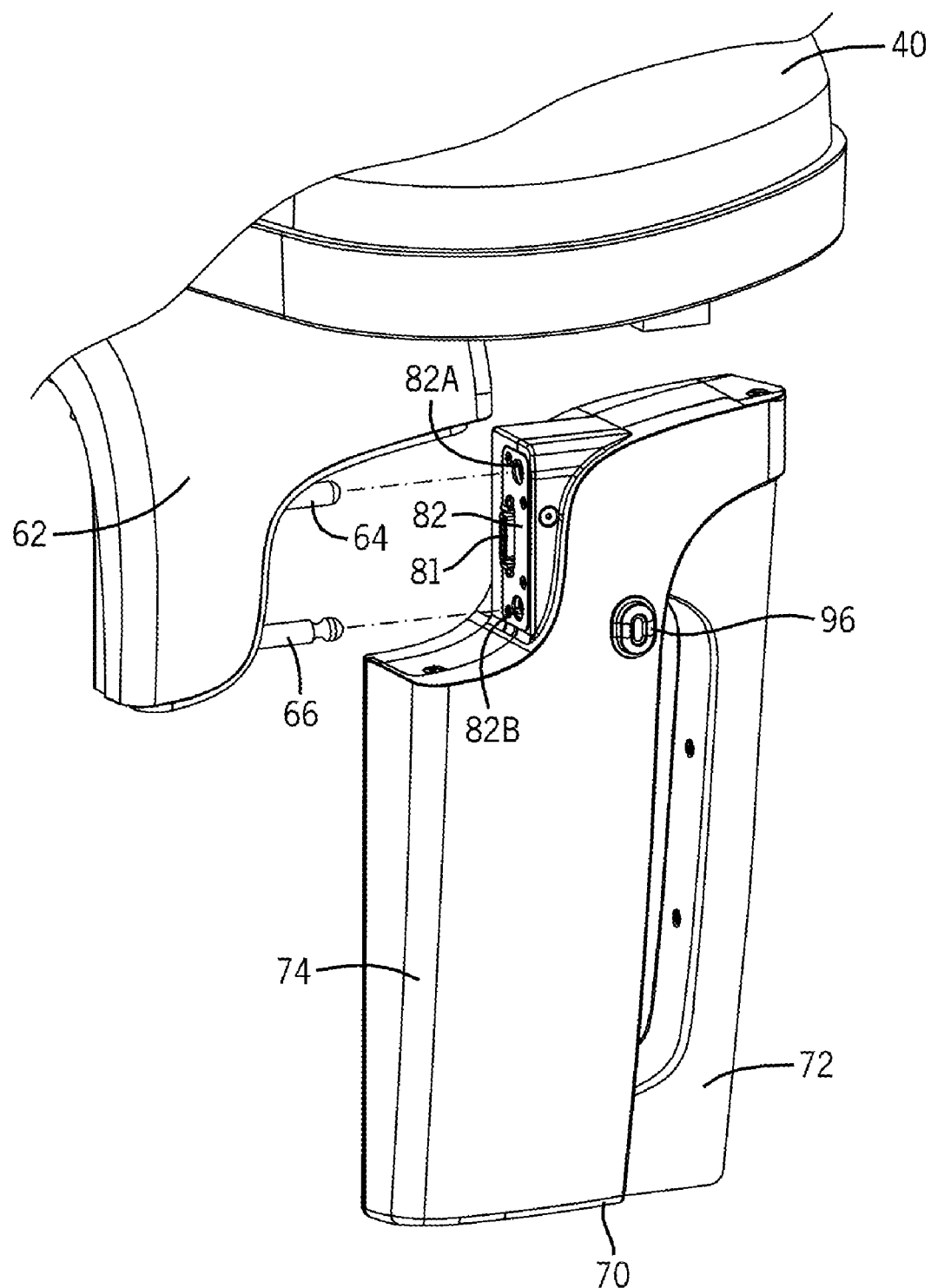
FIG. 4 is rear perspective view of a removable sensor detached from a C-arm portion of a panoramic dental radiation imaging machine.

As mentioned above, the radiation system 10 includes a primary electrical connection system 80, which includes an electronic connector 81 positioned on sensor body 70, and a matching electronic connector 68 for engaging with electronic connector 81. Matching connector 68 is mounted to mounting portion 62, between top connector pin 64 and bottom connector pin 66. Thus when sensor body 70 is attached to C-arm 60, the two parts of primary electrical connection 80, which are electronic connector 81 and matching electronic connector 68, are connected together. In the embodiment shown, particularly in FIG. 8B, primary electrical connection system 80 is formed by the two parts of an MDR connector, but many other types of connectors are also possible and available, including but not limited to card edge connectors and pin-type connectors. The primary electrical connection system 80 provides the power and signal connections to the radiation sensor 71 inside the sensor body 70. A corresponding mounting portion of a combination cephalometric/panoramic radiation system 110, shown in FIG. 3, would be used to connect sensor body 70 to the cephalometric arm 160 of the combination system, such that the sensor body is easily movable from the C-arm 60, that is, in use as a panoramic radiation system, to the cephalometric arm 160, and back.

In all known sensor systems, the sensor body 70 contains a very expensive radiation sensor 71, which is very sensitive to electrostatic discharge (ESD). It is preferable therefore that the case be factory-sealed as it is required for repair personnel to take special care in handling the internal electronics. Thus, for nearly every repair, the entire sensor body 70, containing the sensor unit 71, is required to be returned back to the factory, adding cost and down time. Assuming the sensor body 70 is removed from the C-arm 60 repeatedly, the part most subject to wear and failure is the primary electrical connection system 80. Adding the feature of field-replacement of the primary electrical connection system 80, combined with low-level diagnostic capabilities as to the sensor unit 71 without opening the case, provides substantial advantages for field diagnosis and repair, decreasing overall cost and minimizing down time. The present invention provides an electrical connection system that can be replaced without opening the sensor body 70, that is, a field-replaceable electrical connection system.

Figure 8A:
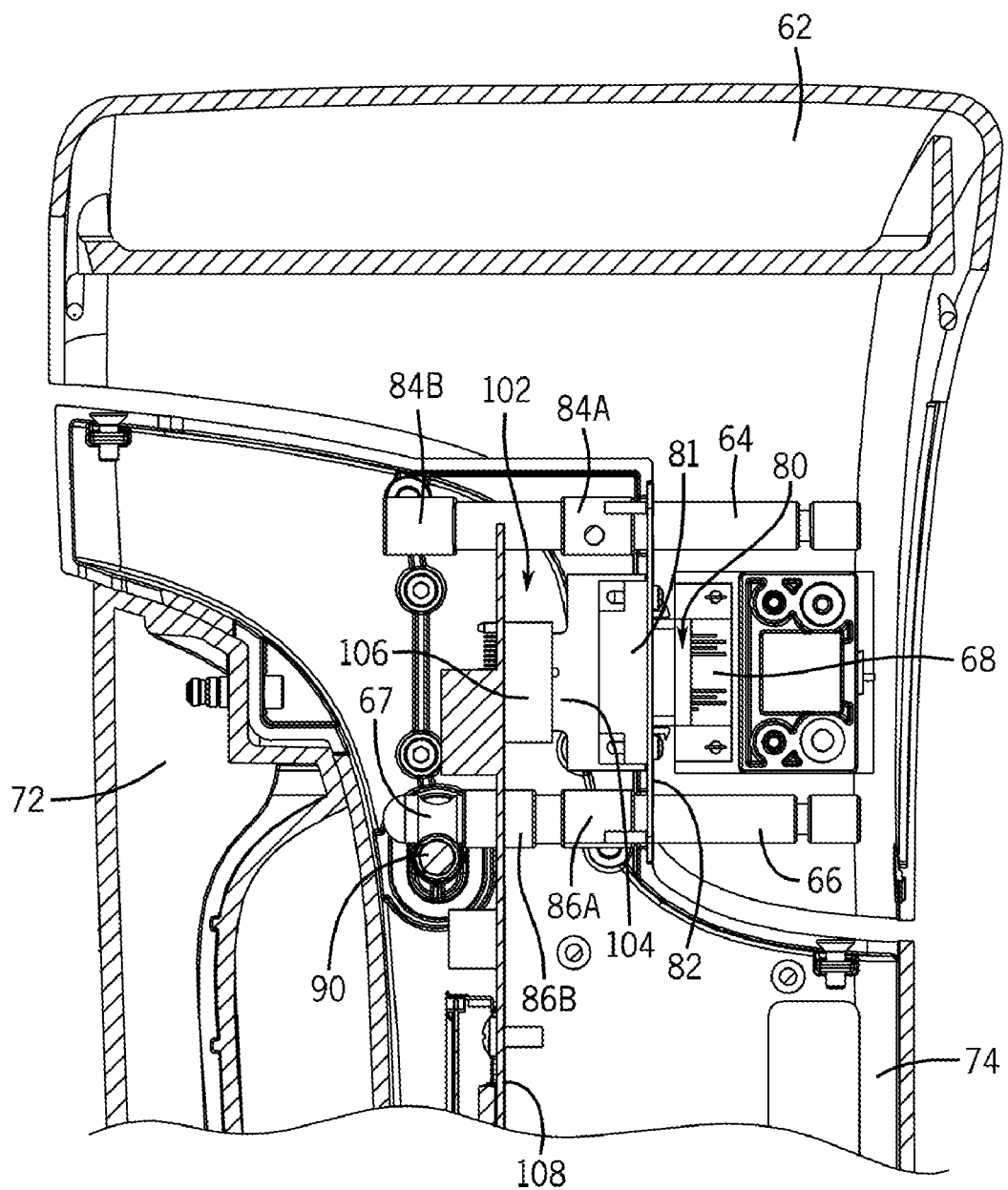
FIG. 8A is a cross-section along line 8A-8A in FIG. 2 with a removable sensor attached to a C-arm and showing a locking pin in position for release of bottom connector pin and detachment of removable sensor.
Figure 8B:
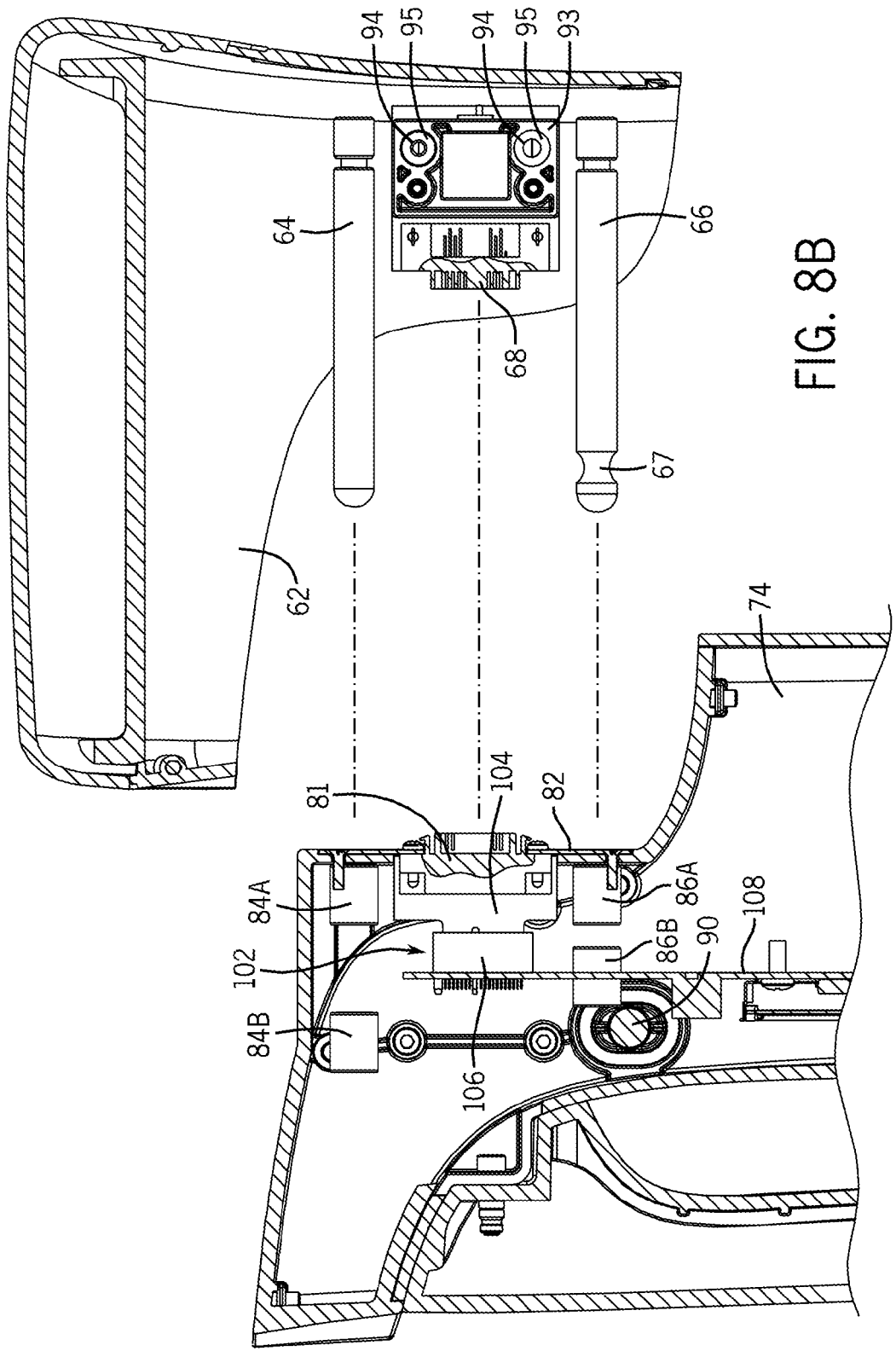
FIG. 8B is a view similar to FIG. 8A with the removable sensor detached from the C-arm.

To further facilitate disconnection and re-connection of the sensor unit 71 with the C-Arm 60, referring mostly to FIG. 8B, the matching electronic connector 68 is physically mounted to mounting portion 62 by means of a flexible or slightly movable connection, so that if electronic connector 81 and matching electronic connector 68 are misaligned by a small amount, they can still be engaged. There are a number of ways to advantageously accomplish this flexible connection. In the most preferred embodiment, matching connector 68 is physically connected to a printed circuit board 93. Printed circuit board 93 is mounted to mounting portion 62 by threaded fasteners 94 passing through openings in the printed circuit board. O-rings 95 are provided to cushion the mounting of the threaded fasteners 94, and thereby printed circuit board 93 and matching connector 68, to mounting portion 62. Thus, because of the O-rings 95, matching connector 68 has some flexibility, in connecting to electronic connector 81.

Figure 8C:
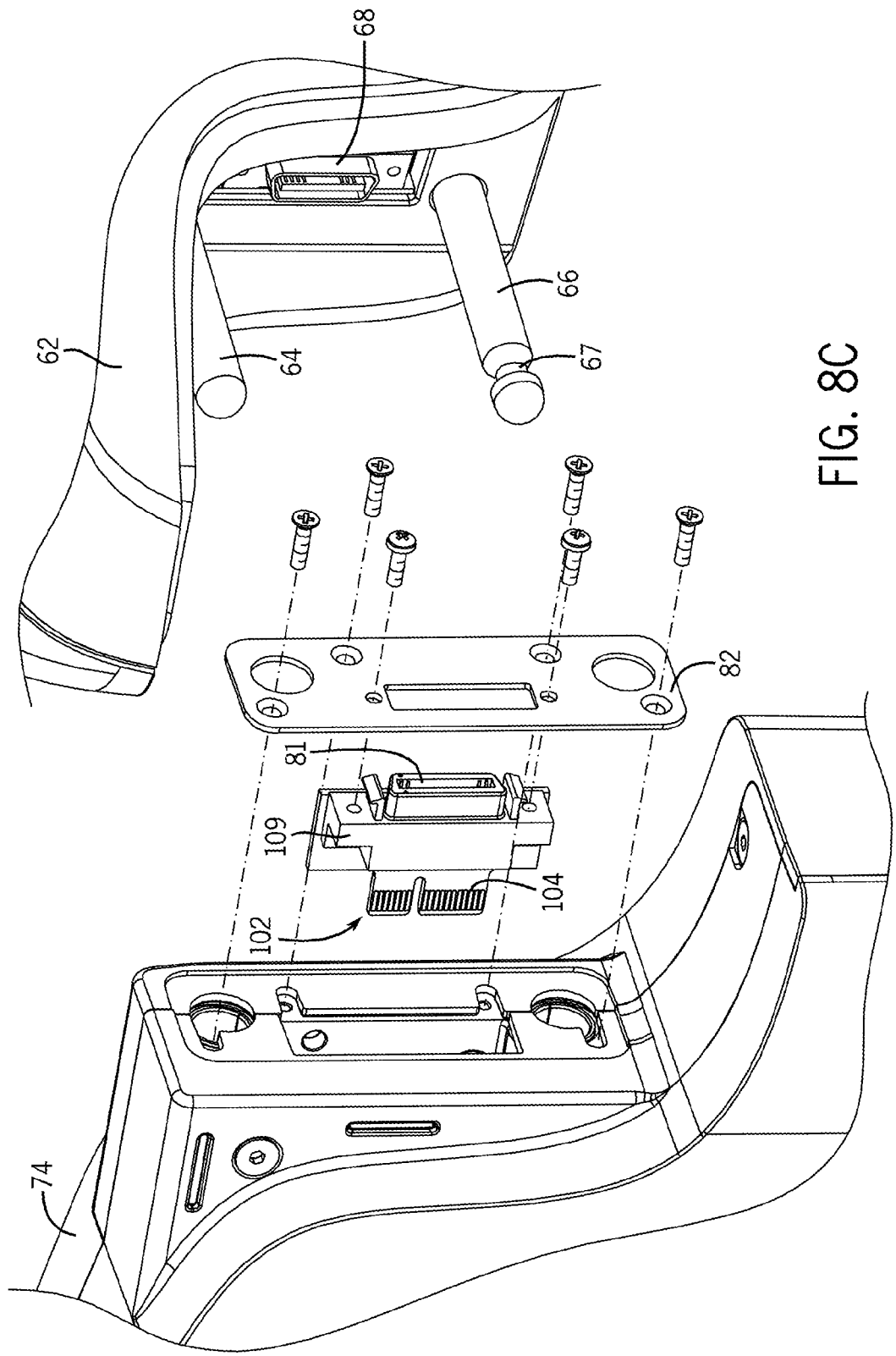
FIG. 8C is a perspective view of the C-arm portion and removable sensor of a panoramic dental radiation imaging machine similar to 8B, enlarged and partially exploded to show detail.

In the most preferred embodiment, the field-replaceable electrical connection system includes a secondary electrical connection system 102, besides the primary electrical connection system 80. As shown best in FIGS. 8A, 8B and 8C, secondary electrical connection system 102 includes a second electronic connector 104 connected to electronic connector 81, and a second matching connector 106, which is in turn connected, by means of suitable circuit board 108, to the sensor unit 71 (FIG. 5) located within the sensor body 70. The preferred embodiment of the secondary electrical connection system 102 is that of a card edge connector, but many other types of connectors are also possible and available, including but not limited to MDR connectors and pin-type connectors. With this system, when the electronic connector 81 wears out, it may be easily replaced, as shown in FIG. 8C, by removal of a few screws and replacement of a small module 109 holding the electronic connector 81 and the second electronic connector 104, and replacement with a new module 109, without the risk or expense of opening the sensor body 70. The number of times the secondary electrical connection system 102 is opened and closed will be much less than the number of times the electronic connector 81 and the matching connector 68 are engaged and disengaged, and so the secondary electrical connection system 102 will have more than a sufficient lifetime to last the life of the overall system 10. Further, the use of an inexpensive and replaceable connection system permits the connector to have more lines of connection, allowing some such lines to be used for diagnostic and testing purposes, both in manufacturing and in the field.

While the current implementation of the primary electrical connection system 80 uses a particular MDR male-female connector pair as it is currently described, the connector gender selection is not limited to the chosen one. Instead, other choices could be used, including reversed pair female-male, or hermaphroditic type of connectors such as the Samtec LST/HLST series of connectors.

As indicated above, radiation sensor unit 71 is located within sensor housing 74. Any suitable radiation sensor unit may be used in this application. In the embodiment shown, the most preferred radiation sensor unit is a CCD sensor with a CCD driver, an analog-front end, a programmable control and processing unit, and programming and diagnostic interfaces, besides a power supply. Other possible sensor implementations may not include all of the mentioned functions, or may add functions such as image processing, storage and other similar functions. Also, it is possible to use sensors other than CCD-type sensors, including CMOS sensors, which eventually may modify the implementation of the sensor driver functions and the analog-front end, or may require additional processing units.

In an alternative embodiment (not shown), connector bearings 84A, 84B, 86A, 86B, electronic connector 81, and locking pin 90 may be mounted within the C-arm 60 for receiving a pair of connector pins 66, 67 coupled to the sensor housing 74. The connection and detachment of the sensor body 70 in this configuration would function in an identical fashion, with the mechanism for releasing the locking pin 90 located on the C-arm 60 rather than the sensor body 70.

Recently three dimensional imaging techniques have been introduced as well, and the current implementation could be extended to those techniques also.

Although the invention has been herein described in what is perceived to be the most practical and preferred embodiments, it is to be understood that the invention is not intended to be limited to the specific embodiments set forth above. Rather, it is recognized that modifications may be made by one of skill in the art of the invention without departing from the spirit or intent of the invention and, therefore, the invention is to be taken as including all reasonable equivalents to the subject matter of the appended claims and the description of the invention herein.

What is claimed is:

1. A removable radiation sensor for being removably connected to a panoramic dental radiation imaging system, the imaging system having a radiation source supported by an upright support, the removable radiation sensor comprising:
    a sensor housing;
    a radiation sensor unit mounted within the housing;
    connector bearings mounted within the housing and sized and positioned therein so as to engage with a pair of connector pins provided for that purpose as part of the upright support;
    an electronic connector system mounted within the housing and sized and positioned therein so as to engage with a matching electronic connector provided for that purpose as part of the upright support, so as to electronically connect the radiation sensor unit to the upright support; and
    a lock mounted to the housing and comprising a locking pin mounted within the housing and selectively slidable between a locked position and an unlocked position, and positioned transverse to the connector bearings, and to the connector pins when the sensor is mounted to the upright support.

2. A removable sensor as recited in claim 1 wherein the locking pin has a groove formed about the periphery of one end thereof, so that when the groove is aligned with a predetermined one of the connector pins, the one connector pin is slidable axially within the bearings and the locking pin is in the unlocked position, whereas when the groove is not aligned with the connector pin, the locking pin engages with a groove formed for that purpose in the connector pin, the locking pin is in the locked position and prevents the connector pin from sliding axially.

3. A removable sensor as recited in claim 2 further comprising a biasing spring, biasing the locking pin toward the locked position.

4. A removable sensor as recited in claim 1 wherein the electronic connector system includes one part of a two-part connector, the matching part being mounted on the upright support, and further comprising a secondary electronic connector pair, one part being connected to the one part of the two-part connector, and the other part being connected to the sensor unit.

5. A removable radiation sensor for being removably connected to a panoramic dental radiation imaging system, the imaging system having a radiation source, a C-arm to which the radiation source is mounted, an overhead arm to which the C-arm is rotatably mounted; and an upright support to which the overhead arm is rotatably mounted, the removable radiation sensor comprising:
    a sensor housing;
    a radiation sensor unit mounted within the housing and capable of receiving and detecting radiation; and
    connector bearings mounted within the housing and sized and positioned therein so as to engage with a pair of connector pins provided for that purpose as part of the C-arm; and
    a lock comprising a locking pin mounted within the housing and selectively slidable between a locked position and an unlocked position, and positioned transverse to the connector bearings, and to the connector pins when the sensor is mounted to the upright support;
    such that the radiation sensor unit is positioned on the C-arm so as to receive and detect radiation from the radiation source.

6. A removable radiation sensor as recited in claim 5 wherein the locking pin has a groove formed about the periphery of one end thereof, so that when the groove is aligned with a predetermined one of the connector pins, the one connector pin is slidable axially within the bearings and the locking pin is in the unlocked position, whereas when the groove is not aligned with the connector pin, the locking pin engages with a groove formed for that purpose in the connector pin, the locking pin is in the locked position and prevents the connector pin from sliding axially.

7. A removable radiation sensor as recited in claim 6 further comprising a biasing spring, biasing the locking pin toward the locked position.

8. A removable sensor as recited in claim 7, wherein the sensor is connected to the C-arm by an electronic connector system, wherein the electronic connector system includes one part of a two-part connector, the matching part being mounted on the upright support, and further comprising a secondary electronic connector pair, one part being connected to the one part of the two-part connector, and the other part being connected to the sensor unit.

9. A panoramic dental radiation imaging system, comprising:
    a radiation source;
    a C-arm to which the radiation source is mounted;
    an overhead arm to which the C-arm is rotatably mounted;
    an upright support to which the overhead arm is rotatably mounted; and
    a radiation sensor removably connected to the C-arm, the removable radiation sensor having a sensor housing, a radiation sensor unit mounted within the housing and capable of receiving and detecting radiation, and connector bearings mounted within the housing and sized and positioned therein so as to engage with a pair of connector pins provided for that purpose as part of the C-arm; and
    a lock comprising a locking pin mounted within the housing and selectively slidable between a locked position and an unlocked position, and positioned transverse to the connector bearings, and to the connector pins when the sensor is mounted to the upright support;

such that the radiation sensor unit is positioned so as to receive and detect radiation from the radiation source.

10. A panoramic dental radiation imaging system in claim 9 wherein the locking pin has a groove formed about the periphery of one end thereof, so that when the groove is aligned with a predetermined one of the connector pins, the one connector pin is slidable axially within the bearings and the locking pin is in the unlocked position, whereas when the groove is not aligned with the connector pin, the locking pin engages with a groove formed for that purpose in the connector pin, the locking pin is in the locked position and prevents the connector pin from sliding axially.

11. A panoramic dental radiation imaging system as recited in claim 10 further comprising a biasing spring, biasing the locking pin toward the locked position.

12. A removable sensor as recited in claim 11, wherein the sensor is connected to the C-arm by an electronic connector system, wherein the electronic connector system includes one part of a two-part connector, the matching part being mounted on the upright support, and further comprising a secondary electronic connector pair, one part being connected to the one part of the two-part connector, and the other part being connected to the sensor unit.

13. A panoramic dental radiation imaging system as recited in claim 10, further comprising a second upright support to which the radiation sensor is attachable, for the purpose of cephalometric imaging.

14. A panoramic dental radiation imaging system, comprising:
 a radiation source;
 a C-arm to which the radiation source is mounted;
 an overhead arm to which the C-arm is rotatably mounted;
 an upright support to which the overhead arm is rotatably mounted; and
 a radiation sensor removably connected to the C-arm, the removable radiation sensor having a sensor housing, a radiation sensor unit mounted within the housing and capable of receiving and detecting radiation, and connector bearings mounted within the C-arm and sized and positioned therein so as to engage with a pair of connector pins provided for that purpose within the housing; and
 a lock comprising a locking pin mounted within the C-arm and selectively slidable between a locked position and an unlocked position, and positioned transverse to the connector bearings, and to the connector pins when the sensor is mounted to the upright support;
 such that the radiation sensor unit is positioned so as to receive and detect radiation from the radiation source.

15. A panoramic dental radiation imaging system in claim 14 wherein the locking pin has a groove formed about the periphery of one end thereof, so that when the groove is aligned with a predetermined one of the connector pins, the one connector pin is slidable axially within the bearings and the locking pin is in the unlocked position, whereas when the groove is not aligned with the connector pin, the locking pin engages with a groove formed for that purpose in the connector pin, the locking pin is in the locked position and prevents the connector pin from sliding axially.

16. A panoramic dental radiation imaging system as recited in claim 15 further comprising a biasing spring, biasing the locking pin toward the locked position.

17. A panoramic dental radiation imaging system as recited in claim 16 wherein the sensor is connected to the C-arm by an electronic connector system, the electronic connector system including one part of a two-part connector, the matching part being mounted on the C-arm, and further comprising a secondary electronic connector pair, one part being connected to the one part of the two-part connector, and the other part being connected to the radiation sensor unit.

* * * * *